United States Patent
Hoeks et al.

(10) Patent No.: US 7,309,735 B2
(45) Date of Patent: *Dec. 18, 2007

(54) METHOD OF MAKING A THERMOPLASTIC COMPOSITION CONTAINING AN ANTISTATIC AGENT

(75) Inventors: Theodorus Lambertus Hoeks, Bergen op Zoom (NL); Chiel Albertus Leenders, Fkjnaart (NL); Robert Dirk van de Grampel, Bergen op Zoom (NL)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,373

(22) Filed: Feb. 13, 2007

(65) Prior Publication Data

US 2007/0129472 A1    Jun. 7, 2007

Related U.S. Application Data

(63) Continuation of application No. 10/966,774, filed on Oct. 15, 2004, now Pat. No. 7,211,690.

(60) Provisional application No. 60/562,010, filed on Apr. 13, 2004.

(51) Int. Cl.
C08J 7/00    (2006.01)
(52) U.S. Cl. ................................................. 524/912
(58) Field of Classification Search ............... None
See application file for complete search history.

(56) References Cited

U.S. PATENT DOCUMENTS

| | | | |
|---|---|---|---|
| 2,732,398 A | 1/1956 | Brice et al. | |
| 3,442,854 A | 5/1969 | Curtis et al. | |
| 4,005,057 A | 1/1977 | Singh et al. | |
| 4,038,258 A | 7/1977 | Singh et al. | |
| 4,093,589 A | 6/1978 | Factor et al. | |
| 4,943,380 A | 7/1990 | Sugiura et al. | |
| 5,021,473 A | 6/1991 | Macholdt et al. | |
| 5,051,330 A * | 9/1991 | Alexandrovich et al. | 430/108.2 |
| 5,112,558 A | 5/1992 | Schad et al. | |
| 5,187,214 A | 2/1993 | Govindan | |
| 5,449,709 A | 9/1995 | Imae et al. | |
| 5,468,793 A | 11/1995 | Ward et al. | |
| 5,468,973 A | 11/1995 | Harada et al. | |
| 5,486,555 A | 1/1996 | Hirata et al. | |
| 5,494,952 A | 2/1996 | Hirata et al. | |
| 5,668,202 A | 9/1997 | Hirata et al. | |
| 6,080,483 A | 6/2000 | Szum et al. | |
| 6,080,488 A | 6/2000 | Hostettler et al. | |
| 6,090,907 A | 7/2000 | Saito et al. | |
| 6,194,497 B1 | 2/2001 | Willems et al. | |
| 6,592,988 B1 | 7/2003 | Thompson et al. | |
| 6,599,966 B2 | 7/2003 | Penning et al. | |
| 6,765,112 B1 | 7/2004 | Schultz | |
| 7,211,690 B2 * | 5/2007 | Hoeks et al. | 562/115 |

FOREIGN PATENT DOCUMENTS

| | | |
|---|---|---|
| EP | 0 170 529 B1 | 2/1986 |
| EP | 0 230 907 A2 | 8/1987 |
| EP | 0 246 825 B1 | 11/1987 |
| EP | 0 266 596 B1 | 5/1988 |
| EP | 0 309 622 B1 | 4/1989 |
| EP | 0 897 950 A2 | 2/1999 |
| EP | 1 462 438 A1 | 9/2004 |
| EP | 1528082 A1 | 5/2005 |
| JP | 1178554 | 7/1989 |

(Continued)

OTHER PUBLICATIONS

European Search Report for EP 98305803; dated Mar. 23, 2000.

(Continued)

Primary Examiner—Paul A. Zucker

(57) ABSTRACT

A method for preparing a thermoplastic composition containing an antistatic agent is described. The antistatic agent is a phosphonium sulfonate salt of generic formula (1)

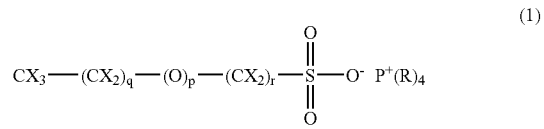

wherein each X is independently a halogen or hydrogen, provided that the molar ratio of halogen to hydrogen is greater than about 0.90; p is 0 or 1 and q and r are integers of 0 to about 7 provided that q+r is less than 8 and that if p is not zero then r is greater than zero; and each R is the same or different hydrocarbon radical containing 1 to about 18 carbon atoms. The phosphonium sulfonate salt is prepared by a method that includes combining in an aqueous medium a compound of generic formula (2)

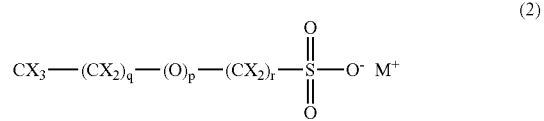

wherein M is Li or Na, and X, q, p, and r are as defined above, with a stoichiometric excess of a compound of the generic formula (3)

$$(R)_4P\text{-}Z \quad (3)$$

wherein Z is a halogen and R is as defined above; and separating the product of formula (1) from the medium. The phosphonium sulfonate salt is then combined with a thermoplastic resin.

11 Claims, 1 Drawing Sheet

FOREIGN PATENT DOCUMENTS

| | | |
|---|---|---|
| JP | 7188539 | 7/1995 |
| JP | 8302165 | 11/1996 |
| WO | WO 2005100307 A1 | 10/2005 |

OTHER PUBLICATIONS

JP 1178554 Publication Date Jul. 14, 1989 (translation of abstract only).

JP 7188539 Publication Date Jul. 25, 1995 (translation of abstract only).

JP 8302165 Publication Date Nov. 19, 1996 (translation of abstract only).

International Search Report; International Application No. PCT/US2005/011756; Mailing Date Oct. 11, 2005.

Gramstad et al., "Perfluoroalkyl Derivatives of Sulphur. Part VI. Perfluoroalkanesulphonic Acids CF3[CF2]nSO3H (n=1-7).", Journal of the Chemical Society, 1957, pp. 2640-2645.

International Search Report; International Application No. PCT/US2005/039369, International Filing Date Oct. 31, 2005; Date of Mailing May 23, 2006.

* cited by examiner

METHOD OF MAKING A THERMOPLASTIC COMPOSITION CONTAINING AN ANTISTATIC AGENT

CROSS-REFERENCE TO RELATED APPLICATIONS

This application is a continuation of U.S. patent application Ser. No. 10/966,774, filed Oct. 15, 2004, now U.S. Pat. No. 7,211,690, which claims the benefit of U.S. Provisional application Ser. No. 60/562,010, filed Apr. 13, 2004. Both applications are hereby incorporated by reference in their entirety.

BACKGROUND OF THE INVENTION

This disclosure relates to a method of making an antistatic agent.

Thermoplastics are useful in the manufacture of articles and components for a wide range of applications, from automotive parts to electronic appliances. Because of their broad use, particularly in electronic applications, it is desirable to provide thermoplastic resins with antistatic agents. Many polymers or blends of polymers are relatively non-conductive, which can lead to static charge build-up during processing and use of the polymer. Charged molded parts, for example, may attract small dust particles, and may thus interfere with a smooth surface appearance, for example by causing a decrease in the transparency of the article. In addition, the electrostatic charge may be a serious obstacle in the production process of such polymers.

Anti-static agents are materials that are added to polymers to reduce their tendency to acquire an electrostatic charge, or, when a charge is present, to promote the dissipation of such a charge. Organic anti-static agents are usually hydrophilic or ionic in nature. When present on the surface of polymeric materials, they facilitate the transfer of electrons and thus eliminate the build up of a static charge. Anti-static agents have also been added to the polymer composition before further processing into articles, and may thus be referred to as "internally applied." Useful anti-static agents applied in this manner are thermally stable and able to migrate to the surface during processing.

A large number of anti-static agents having surfactants as their main constituent have been considered and tried. Many suffer from one or more drawbacks, such as lack of compatibility with the polymer (which interferes with uniform dispersibility), poor heat stability, and/or poor antistatic characteristics. Poor heat resistance in particular can adversely affect the optical properties of engineering thermoplastics such as aromatic polycarbonates.

Particular phosphonium salts of certain sulfonic acids, however, have been shown to be useful antistatic agents. U.S. Pat. No. 4,943,380 discloses reducing the static charge on polycarbonate resins with an anti-static composition containing 90-99.9 weight % of polycarbonate and 0.1-10 weight % of a heat resistant phosphonium sulfonate having the general formula:

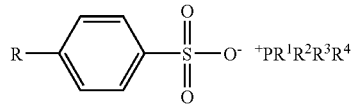

wherein R is a straight or branched chain alkyl group having 1 to 18 carbon atoms; $R_1$, $R_2$ and $R_3$ are the same, each being an aliphatic hydrocarbon having 1 to 8 carbon atoms or an aromatic hydrocarbon group having 6 to 12 carbon atoms; and $R_4$ is a hydrocarbon group having 1 to 18 carbon atoms.

U.S. Pat. No. 6,194,497 discloses antistatic resin compositions, particularly transparent resin compositions, comprising a thermoplastic polymer and a halogenated medium- or short-chain alkylsulfonic acid salt of a tetrasubstituted phosphonium cation. The antistatic agent described therein is prepared by ion exchange of a potassium haloalkylsulfonate to produce the corresponding acid. The haloalkylsulfonic acid is then reacted with tetrabutylphosphonium hydroxide to product the antistatic agent.

An advantage of this synthesis is that use of an ion exchange step during synthesis results in a product that is very pure, i.e., contains little to no halogenated compounds that may ultimately lead to degradation of resins such as polycarbonates. However, while suitable for its intended purposes, this particular synthesis also has a number of drawbacks. For example, use of an ion exchange step increases the expense of the process, and may lead to the production of waste requiring disposal procedures. The synthesis also uses the potassium salt as a starting product, which is prepared from the corresponding sulfonylfluoride. Since the solubility of potassium peralkylsulfonates is relatively low, e.g., on the order of 5% at 20° C., a water/ethanol mixture is needed in the ion exchange. The flammability of ethanol requires the implementation of significant safety precautions during the synthesis. In addition, selecting the appropriate water/ethanol ratio is also important. An excess of alcohol may render the final product soluble in the reaction solvent, such that isolation of the product may require a further extraction step.

There accordingly remains a demand in the art for more efficient processes, particularly one-step processes, for making phosphonium sulfonate antistatic agents, as well as thermoplastic resin compositions that incorporate these antistatic agents. It would further be desirable for such processes to produce the antistatic agent in good yields without having a detrimental effect on the safety of the process and/or the purity of the product.

BRIEF SUMMARY OF THE INVENTION

The above-described and other deficiencies of the art are met by a method of making a phosphonium sulfonate salt of formula (1):

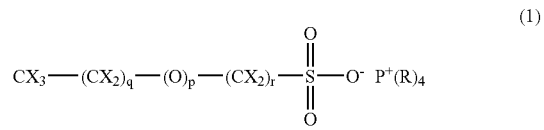

wherein each X is independently a halogen or hydrogen, provided that the molar ratio of halogen to hydrogen is greater than about 0.90; p is 0 or 1 and q and r are integers of 0 to about 7, provided that q+r is less than 8 and that if p is not zero then r is greater than zero; and each R is independently a hydrocarbon radical having 1 to about 18 carbon atoms, the method comprising combining in an aqueous medium a compound of the formula (2):

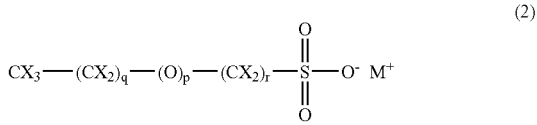

(2)

wherein M is Li or Na, and X, q, p, and r are as defined above, with a compound of the formula (3):

$$(R)_4P\text{-}Z \quad (3)$$

wherein Z is a halogen and R is as defined above; and separating the product of formula (1) from the aqueous medium.

In another embodiment, a method of making the phosphonium sulfonate salt of formula (1) comprises first combining in an aqueous medium, a compound of the formula (4)

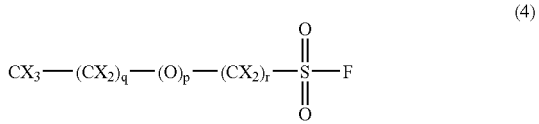

(4)

with a stoichiometric excess of a compound of the generic formula (5):

$$(R)_4P\text{—}OH \quad (5)$$

wherein X, p, q, r, and R have the same meanings as in formula (1); and separating the product of formula (1) from the aqueous medium.

In another embodiment, a method of making the phosphonium sulfonate salt of formula (1) comprises combining in an aqueous medium sodium hydroxide and/or lithium hydroxide, a compound of the generic formula (4) above, and a compound of the generic formula (3) above, wherein X, q, p, r, and R are as defined above; and separating the phosphonium sulfonate of formula (1) from the aqueous medium.

Another embodiment comprises an antistatic agent of formula (1) made by one of the foregoing methods.

In another embodiment there are provided thermoplastic compositions comprising a thermoplastic polymer and an antistatic agent made by one of the foregoing methods.

DETAILED DESCRIPTION OF THE INVENTION

Figure 1:
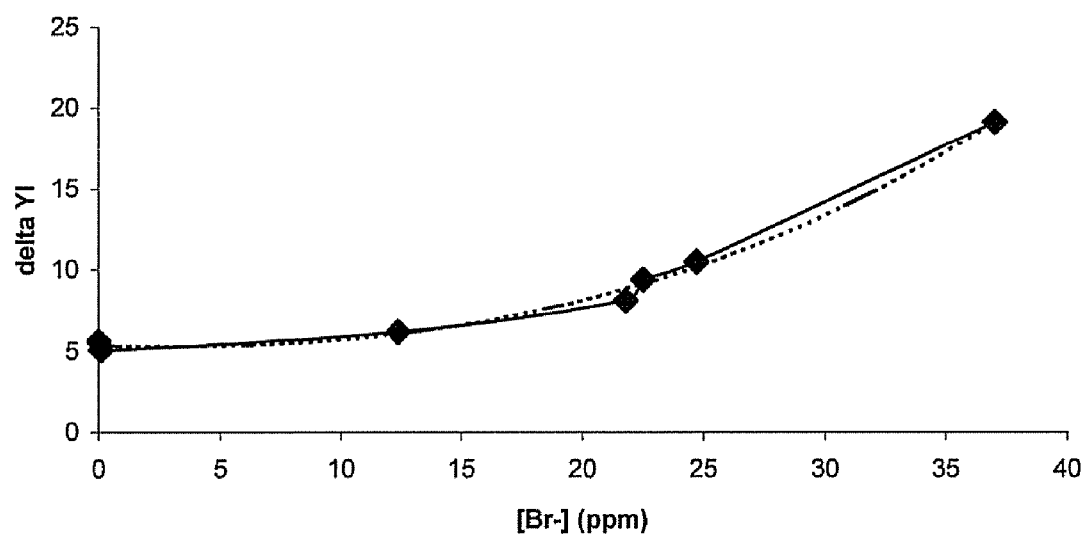
FIG. 1 is a graph of the change in yellowness index (Delta YI) after 926 hours aging at 130° C. as a function of bromide concentration ([Br$^-$]) in the polycarbonate.

It has been unexpectedly found by the inventors hereof that a phosphonium haloalkylsulfonate salt suitable for use as antistatic agent may be readily obtained in aqueous medium in one step from the corresponding tetraalkylphosphonium halide and lithium or sodium haloalkylsulfonate salt. Alternatively, the phosphonium haloalkylsulfonate salt may be obtained in aqueous medium in one step from the corresponding tetraalkylphosphonium halide or hydroxide and the haloalkylsulfonyl fluoride. The reactants are readily available, and use of water as the reaction solvent expedites isolation of the product. Thus, in a surprising and highly advantageous feature, the inventors hereof have found that a simple mixing of the reactants may result in a precipitation of the targeted anti-static molecule in high yields.

In general, the phosphonium haloalkylsulfonate salts are of the generic formula (1):

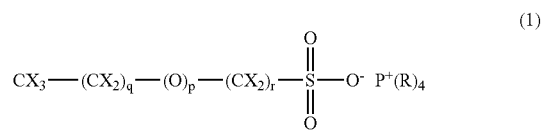

(1)

wherein X is independently selected from halogen or hydrogen, provided that the molar ratio of halogen to hydrogen is greater than about 0.90. The halogens may be independently selected from bromine, chlorine, fluorine, and iodine. Specifically, the halogen is fluorine.

Further in formula (1), p is zero or one, and q and r are integers of 0 to about 7, provided that q+r is less than 8 and that if p is not zero then r is greater than zero. In one embodiment, p is zero.

Each R in formula (1) is independently a hydrocarbon radical containing 1 to about 18 carbon atoms, that is, each R is the same or different, and may be a straight or branched chain aliphatic hydrocarbon radical containing 1 to about 18 carbon atoms, or an aromatic hydrocarbon radical containing 6 to about 18 carbon atoms. As used herein, an "aromatic" radical is inclusive of fully aromatic radicals, aralkyl radicals, and alkaryl radicals. In one embodiment, three of the R groups in the organic phosphonium cation may be the same aliphatic hydrocarbon radical containing 1 to about 8 carbon atoms or aromatic hydrocarbon radical containing 6 to about 12 carbon atoms, while the fourth R group may be a hydrocarbon radical containing 1 to about 18 carbon atoms.

The antistatic agent may thus be a highly halogenated phosphonium sulfonate salt containing an organic sulfonate anion and a tetrasubstituted organic phosphonium cation. Specific examples are perfluorinated salts, but due to the production method of the fluorination (electrolysis) sometimes only partly fluorinated compounds are formed.

Specific examples of suitable organic sulfonate anions include perfluoromethane sulfonate, perfluoroethane sulfonate, perfluoropropane sulfonate, perfluorobutane sulfonate, perfluoropentane sulfonate, perfluorohexane sulfonate, perfluoroheptane sulfonate, and perfluorooctane sulfonate. Combinations of the foregoing may also be present.

Examples of specific phosphonium cations include cations such as tetramethyl phosphonium, tetraethyl phosphonium, tetra-n-propyl phosphonium, tetraisopropyl phosphonium, tetrabutyl phosphonium, triethylmethyl phosphonium, tributylmethyl phosphonium, tributylethyl phosphonium, trioctylmethyl phosphonium, trimethylbutyl phosphonium, trimethyloctyl phosphonium, trimethyllauryl phosphonium, trimethylstearyl phosphonium, triethyloctyl phosphonium, tetraphenyl phosphonium, triphenylmethyl phosphonium, triphenylbenzyl phosphonium, and tributylbenzyl phosphonium. Combinations of the foregoing may also be present.

In one embodiment there is provided a method for making the phosphonium sulfonates of formula (1) comprising combining, in an aqueous medium, a compound of the formula (2):

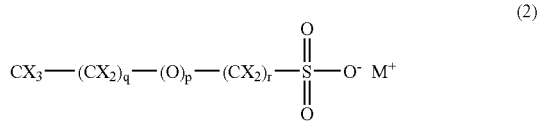

wherein M is an alkali metal selected from lithium (Li) or sodium (Na), and X, q, p, and r are as defined above, with a stoichiometric excess of a compound of the formula (3):

wherein Z is a halogen and R is as defined above; and separating the product of formula (1). Specifically Z may be bromine or chlorine.

In one manner of proceeding, the process may comprise dissolving a perhaloalkylsulfonate sodium or lithium salt of formula (2) in an aqueous medium. The aqueous medium may be substantially free of a cosolvent such as ethanol, for example. As used herein, "an aqueous medium" means a solution, dispersion, or suspension in water. Further as used herein, an aqueous medium "substantially free of a cosolvent" means an aqueous medium containing less than about 1, specifically less than about 0.5, and more specifically less than about 0.1 volume percent cosolvent. While the use of a cosolvent is possible, and necessary in the case of the potassium salts, the use of water substantially free of a cosolvent results in a higher purity product, and avoids the safety concerns that arise from use of volatile solvents. Suitable cosolvents, when used, aid in dissolving the sulfonate alkali salts, and include lower alcohols such as methanol, ethanol, and the like, and chlorinated solvents such as dichloromethane, and the like. Mixtures of cosolvents may be used.

The aqueous medium containing the perhaloalkylsulfonate alkali salt may then be reacted with a tetrasubstituted phosphonium halide. The order of addition does not appear to be important, i.e., reaction may also be accomplished by, for example, dissolving the tetrasubstituted phosphonium halide in an aqueous medium and then adding the perhaloalkylsulfonate alkali salt; by simultaneously dissolving and mixing the reactants; by separately dissolving then mixing the reactants; or the like. The phosphonium sulfonate salts obtained herein may be obtained by using mixtures of perhaloalkylsulfonate alkali salts and tetrasubstituted phosphonium halides.

The processes may be conducted at a broad range of temperatures and reaction times, and will depend on the particular reactants used, cosolvent (if present), desired yields, desired purity, cost, convenience, ease of manufacture, and like considerations. For example, temperatures for the various processes may generally be about 10° C. to about 100° C., specifically about 20° C. to about 95° C., more specifically about 30° to about 90° C. In one embodiment, the reaction is conducted at room temperature or ambient temperature, which may generally be about 20° C. to about 25° C. Likewise, reaction times may vary, but generally may be about 5 minutes to about one day, specifically about 30 minutes to about 12 hours, or more specifically about 60 minutes to about 4 hours. These temperatures and times may be varied greatly and may be determined by those of ordinary skill in the art.

The tetrasubstituted phosphonium halide may used in an at least equimolar amount relative to the perhaloalkylsulfonate salt, and more specifically, the molar ratio of the perhaloalkylsulfonate salt of formula (2) to the tetrasubstituted phosphonium halide of formula (3) may be about 1:1.001 to about 1:1.5, specifically about 1:1.002 to about 1:1.1, more specifically about 1:1.005 to about 1:1.015. The optimum ratio may vary depending on the particular reactants, temperature, cosolvent(s) (if present), and time, and is readily determined by one of ordinary skill in the art.

In another embodiment, the molar ratio of the perhaloalkylsulfonate salt of formula (2) to the tetrasubstituted phosphonium halide of formula (3) may be about 1.001:1 to about 1.5:1, specifically about 1.002:1 to about 1.1:1, more specifically about 1.005:1 to about 1.015:1. The optimum ratio may vary depending on the particular reactants, temperature, cosolvent(s) (if present), and time, and is readily determined by one of ordinary skill in the art.

In a highly advantageous feature, the reactants and aqueous medium are selected so that phosphonium sulfonate salt (1) precipitates from the aqueous medium at high purity, and may be isolated from impurities, in particular halogen-containing impurities, by simple filtration and washing. It is desirable to remove halogen-containing impurities in particular (such as the tetrasubstituted phosphonium bromide and/or chloride) since these impurities are known to degrade resins such as polycarbonate. Removal of the impurities is readily and efficiently accomplished by washing with water, since the impurities are soluble in water, while the desired product is not.

In another embodiment there is provided a method for making the phosphonium sulfonate of formula (1) comprising combining in an aqueous medium a sulfonylfluoride of the generic formula (4):

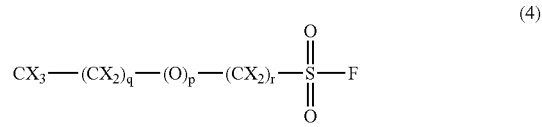

wherein X, p, q, and r have the same meanings as above, with a stoichiometric excess of a tetrasubstituted phosphonium hydroxide of the formula (5):

wherein R is as defined above; and separating the product of formula (1) from the aqueous medium. In one embodiment, the reactants and aqueous medium are selected so that phosphonium sulfonate salt precipitates from the aqueous medium.

In this embodiment the phosphonium sulfonate salt of formula (1) may be produced in a one-step process, which may comprise reacting sulfonylfluoride (4) with tetrasubstituted phosphonium hydroxide (5) in a single vessel in an aqueous medium. Thus, compound (4) may be dispersed or dissolved in an aqueous medium containing a cosolvent or substantially free of a cosolvent such as is described above, to which a tetrasubstituted phosphonium hydroxide (5) is then added. The order of addition does not appear to be important, i.e., reaction may also be accomplished by, for example, dissolving the tetrasubstituted phosphonium hydroxide (5) in an aqueous medium and then adding the sulfonylfluoride (4), or by simultaneously dissolving/dispersing and mixing the reactants. Combinations of different sulfonylfluorides (4) and/or different tetrasubstituted phosphonium hydroxide (5) may be reacted.

As above, a broad range of reaction times, temperatures and other process conditions may be used, but room temperature is preferred for ease of manufacture. Generally the tetrasubstituted phosphonium hydroxide (5) is used in an amount of at least about 2 moles per mole of sulfonylfluoride (4), and more specifically, the molar ratio of the compound of formula (4) to the phosphonium hydroxide of formula (5) may be about 1:2.01 to about 1:3, specifically about 1:2.1 to about 1:2.7, or more specifically of about 1:2.2 to about 1:2.6. The optimum ratio may vary depending on the particular reactants, temperature, cosolvent(s) (if present) and time, and is readily determined by one of ordinary skill in the art.

In another embodiment there is provided a method for making the phosphonium sulfonate salts of formula (1) comprising combining, in an aqueous medium, a sulfonylfluoride of formula (4), a tetrasubstituted phosphonium halide of formula (3), and an alkali metal or alkaline earth metal base; and separating the phosphonium sulfonate of formula (1) from the aqueous medium. Suitable bases include, for example, alkaline hydroxides such as potassium hydroxide, sodium hydroxide, lithium hydroxide, magnesium hydroxide, and the like. Mixtures may also be used. Potassium hydroxide, sodium hydroxide, and/or lithium hydroxide are preferred. In one embodiment, the reactants and aqueous medium are selected so that phosphonium sulfonate salt precipitates from the aqueous medium.

Again, the order of addition does not appear to be important. Thus, the components may be mixed simultaneously, or tetrasubstituted phosphonium halide (3) may be added to an aqueous solution/dispersion of the base, and this medium/dispersion added to a solution/dispersion of sulfonyl fluoride (4). In still another embodiment, sulfonylfluoride (4) and the base are combined, and allowed to react for a time effective to form the alkali sulfonate salt (2). Phosphonium halide (3) is then added to the medium to form the product without isolation of alkali sulfonate salt (2). This method is simple, efficient, and minimizes time and materials. Alternatively, alkali sulfonate salt (2) may be isolated and redissolved with or without cosolvent prior to addition of phosphonium halide (3).

A broad range of reaction times, temperatures, and other process conditions may be used, but about 25° C. (room temperature) to about 100° C. is preferred for ease of manufacture. Optimal reactant ratios are readily determined by one of ordinary skill in the art, and may be, for example, those described above.

Phosphonium sulfonate salt that may be made by the processes described herein include those having the general formula (6):

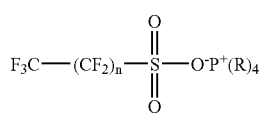

(6)

wherein F is fluorine; n is an integer of 0 to about 7, S is sulfur; and each R is the same or different aliphatic hydrocarbon radical containing 1 to about 18 carbon atoms or an aromatic hydrocarbon radical containing 6 to about 18 carbon atoms. In one embodiment, three of the R groups in the organic phosphonium cation may be the same aliphatic hydrocarbon radical containing 1 to about 8 carbon atoms or aromatic hydrocarbon radical containing 6 to about 12 carbon atoms, while the fourth R group may be a hydrocarbon radical containing 1 to about 18 carbon atoms. Anti-static compositions comprising fluorinated phosphonium sulfonates of formula (6) as the principle component thereof may be used in many different ways to make use of their anti-static, compatibility and heat resistance characteristics, for example, in providing such anti-static characteristics to thermoplastic resins. Suitable thermoplastic resins include but are not limited to polycarbonate, polyetherimide, polyester, polyphenylene ether/polystyrene blends, polyamides, polyketones, acrylonitrile-butadiene-styrenes (ABS), or combinations comprising at least one of the foregoing polymers. The phosphonium sulfonate salts are low melting semi-solid materials, and as such, they may be handled as a molten liquid. Some embodiments of the present disclosure are solid crystalline materials at room temperature (about 15 to about 25° C.) and are easy to weigh, handle, and add to the above-described thermoplastic resins.

In addition to the thermoplastic resin, the thermoplastic composition may include various additives ordinarily incorporated in resin compositions of this type. Mixtures of additives may be used. Such additives may be mixed at a suitable time during the mixing of the components for forming the composition. Examples of suitable additives are impact modifiers, fillers, heat stabilizers, antioxidants, light stabilizers, plasticizers, mold release agents, UV absorbers, lubricants, pigments, dyes, colorants, blowing agents, anti-drip agents, and flame-retardants.

A common way to practice this method is to add the agent directly to the thermoplastic resin and to mix it at the time of polymer production or fabrication. It may be processed by traditional means, including extrusion, injection, molding, compression molding or casting. The thermoplastic compositions may be manufactured by methods generally available in the art, for example, in one embodiment, in one manner of proceeding, powdered thermoplastic resin, antistatic agent, and/or other optional components are first blended, optionally with chopped glass strands or other fillers in a Henschel high speed mixer. Other low shear processes including but not limited to hand mixing may also accomplish this blending. The blend is then fed into the throat of a twin-screw extruder via a hopper. Alternatively, one or more of the components may be incorporated into the composition by feeding directly into the extruder at the throat and/or downstream through a sidestuffer. Such additives may also be compounded into a masterbatch with a desired polymeric resin and fed into the extruder. The extruder is generally operated at a temperature higher than that necessary to cause the composition to flow. The extrudate is immediately quenched in a water bath and pelletized. The pellets, so prepared, when cutting the extrudate may be one-fourth inch long or less as desired. Such pellets may be used for subsequent molding, shaping, or forming.

The quantity of the phosphonium sulfonate salt added to thermoplastic resin is an amount effective to reduce or eliminate a static charge and may be varied over a range. It has been found that if too little of the anti-static substituted phosphonium sulfonate salt is added to the resin, there still may be a tendency for static charge to build up on an article made of the resin. If the loadings of the anti-static additive become too high, the addition of these quantities is uneconomical, and at some level it may begin adversely to affect other properties of the resin. Thermoplastic compositions with enhanced antistatic properties may be obtained using about 0.01 to about 10 weight percent (wt %), specifically about 0.2 to about 2.0 wt %, more specifically about 0.5 to about 1.5 wt of the anti-static agent with about 90 to about 99.99 wt %, specifically about 99 to about 99.8 wt %, more specifically about 98.5 to about 99.5 wt % polymer, based on the total weight of anti-static agent and polymer. In one embodiment, in order to obtain a favorable result by such an internal application method in transparent polycarbonate grades, the antistatic agent is used generally in amounts of about 0.01 to about 3.0, specifically about 0.1 to about 1.5 weight percent (wt. %) with respect to the molding composition or specifically in amounts of about 0.4 to about 0.8 wt. %. The antistatic agents provided herein are more strongly resistant against heat and may be added in lower quantities than the traditional ionic surfactants, e.g. phosphonium allcyl sulfonates, and the resin compositions have good transparency and mechanical properties.

The above-described phosphonium salts may further be used to prepare thermoplastic polymer compositions having improved heat stability. In one embodiment a polycarbonate composition comprising an antistatic agent manufactured by one of the above processes has a Yellowness Index of less than about 15, specifically less than about 10, more specifically less than about 8, and even more specifically less than about 6 after aging at 130° C. for 936 hours.

The thermoplastic composition comprising the antistatic agent may be used to form articles such as, for example, computer and business machine housings such as housings for monitors, handheld electronic device housings such as housings for cell phones, electrical connectors, and components of lighting fixtures, ornaments, home appliances, roofs, greenhouses, sun rooms, swimming pool enclosures, carrier tapes for semiconductor package material, automobile parts, and the like.

The thermoplastic compositions may be converted to articles using processes such as film and sheet extrusion, injection molding, gas-assist injection molding, extrusion molding, compression molding, and blow molding. Film and sheet extrusion processes may include and are not limited to melt casting, blown film extrusion and calendaring. Co-extrusion and lamination processes may be used to form composite multi-layer films or sheets. Single or multiple layers of coatings may further be applied to the single or multi-layer substrates to impart additional properties such as scratch resistance, ultra violet light resistance, aesthetic appeal, and the like. Coatings may be applied through application techniques such as rolling, spraying, dipping, brushing, or flow coating. Films or sheets may alternatively be prepared by casting a solution or suspension of the thermoplastic composition in a suitable solvent onto a substrate, belt, or roll followed by removal of the solvent.

Oriented films may be prepared through blown film extrusion or by stretching cast or calendared films in the vicinity of the thermal deformation temperature using conventional stretching techniques. For instance, a radial stretching pantograph may be employed for multi-axial simultaneous stretching; an x-y direction stretching pantograph can be used to simultaneously or sequentially stretch in the planar x-y directions. Equipment with sequential uniaxial stretching sections can also be used to achieve uniaxial and biaxial stretching, such as a machine equipped with a section of differential speed rolls for stretching in the machine direction and a tenter frame section for stretching in the transverse direction.

The thermoplastic compositions of the invention may also be converted to a multiwall sheet comprising a first sheet having a first side and a second side, wherein the first sheet comprises a thermoplastic polymer, and wherein the first side of the first sheet is disposed upon a first side of a plurality of ribs; and a second sheet having a first side and a second side, wherein the second sheet comprises a thermoplastic polymer, wherein the first side of the second sheet is disposed upon a second side of the plurality of ribs, and wherein the first side of the plurality of ribs is opposed to the second side of the plurality of ribs.

The films and sheets described above may further be thermoplastically processed into shaped articles via forming and molding processes including, for example thermoforming, vacuum forming, pressure forming, injection molding, and compression molding. Multi-layered shaped articles may also be formed by injection molding a thermoplastic resin onto a single or multi-layer film or sheet substrate, for example by providing a single or multi-layer thermoplastic substrate having optionally one or more colors on the surface, for instance, using screen printing or a transfer dye; conforming the substrate to a mold configuration such as by forming and trimming a substrate into a three dimensional shape and fitting the substrate into a mold having a surface which matches the three dimensional shape of the substrate; injecting a thermoplastic resin into the mold cavity behind the substrate to (i) produce a one-piece permanently bonded three-dimensional product or (ii) transfer a pattern or aesthetic effect from a printed substrate to the injected resin and remove the printed substrate, thus imparting the aesthetic effect to the molded resin.

Those skilled in the art will also appreciate that known curing and surface modification processes, including but not limited to heat-setting, texturing, embossing, corona treatment, flame treatment, plasma treatment, and/or vacuum deposition may further be applied to the above articles to alter surface appearances and impart additional functionalities to the articles.

Accordingly, another embodiment of the invention relates to articles, sheets, and films prepared from the above thermoplastic compositions.

The above processes may be used to form phosphonium salts (1) in an expedited manner and in high purity. In one embodiment, the total amount of ionic impurities is less than about 650 parts per million (ppm), more specifically less than about 500 ppm, even more specifically less than about 100 ppm, more specifically less than about 50 ppm, and most specifically less than about 10 ppm. In another embodiment, the products contain less than about 5 ppm of alkali metals, preferably less than about 4 ppm of alkali metals. In another embodiment, the products contain less than about 500 ppm, preferably less than about 100 ppm, more preferably less than about 50 ppm, and most preferably less than about 10 ppm of halide. Other ionic contaminants, for example phosphate or sulfate, are individually present in amounts of less than about 100 ppm, preferably less than about 50 ppm, most preferably less than about 10 ppm.

The methods are further illustrated by the following non-limiting examples.

EXAMPLES

Differential scanning calorimetry (DSC) measurements were conducted by scanning the sample from 50° C. to 100° C. with a scan speed of 10° C./min. Thermal gravimetric analysis (TGA) was conducted by scanning the sample from 50° C. to 600° C. with a scan speed of 10° C./min. Ion content of the salts was determined by ion chromatography. Yellowness index (YI) was determined using a Gretag MacBeth color-eye 7000A using propalette software.

In the following examples, "MQ water" refers to water deionized and processed through a MilliQ® System. (MilliQ® is a trademark of Millipore Corporation.) "TBPBr" refers to tetrabutyl phosphonium bromide.

Example 1

First, 5.00 gram (MW 302, 16.55 mmol) of perfluorobutane sulfonyl fluoride ("A") is weighed in a 100-mL 2-neck roundbottom flask, stirred with a magnetic stirrer and refluxed therein, in an oil bath at 85° C.

Next, 0.95 grams of lithium hydroxide (LiOH) (24.83 mmol) is added and dissolved in 25 mL MQ water and slowly added to A. This is followed by letting the mixture reflux for an hour and then adding 25 mL MQ water and stirrring. Then the undissolved residue is filtered off, and collected in another 100-mL 2-neck roundbottom flask, and reheated in an oil bath at 85° C. once more. Next 8.43 gram TBPBr (24.83 mmol) is dissolved in 25 mL MQ water and is added slowly to the filtrate and the product antistatic agent is formed. After all the dissolved TBPBr is added the mixture is stirred for another 15 minutes. Then the mixture is cooled, preferably in an ice/water bath, and then the water is decanted. Next, 100 mL of MQ water is added and stirred for 15 minutes while heating in an oil bath at 85° C. The mixture is next cooled to room temperature and the product is isolated by filtration and is flushed with 25 mL MQ water. The product is dried in a vacuum drying oven at 50° C. The theoretical yield is 9.24 grams of antistatic agent; 3.8 g were obtained.

Example 2

First, 54.8 grams (180.837 mmol) of lithium perfluorobutane sulfonate ("Li Rimar") is added to and dissolved in 300 mL MQ water at room temperature and 60.8 grams (179.062 mmol) of TBPBr is added to and dissolved in 200 mL MQ water at room temperature. The TBPBr solution is filtered and then poured gradually into the Li Rimar salt solution while stirring with a propeller stirrer, and the product antistatic agent is formed. After all the TBPBr is added the reaction mixture is stirred for 15 minutes more. At the end of the reaction the product antistatic agent is isolated by filtration and flushed with 50 mL MQ water to remove most impurities. Further purification is accomplished by suspending the product antistatic agent in MQ water and heating it up to 80° C., stirring it for a few minutes and cooling the mixture so that the product antistatic agent crystallizes again. The product antistatic agent can then be isolated by filtration and dried in a vacuum drying oven at 50° C. The theoretical yield is 100.0 grams of antistatic agent; 87.1 grams were obtained.

Example 3

First 5.00 grams (MW 302, 16.55 mmol) of perfluorobutane sulfonyl fluoride ("A") is weighed in a 100-mL 2-neck roundbottom flask, stirred with a magnetic stirrer and refluxed in an oil bath at 85° C.

Next a 32 wt % NaOH solution is slowly added, that is 2.4 times the amount of A. That is, 39.72 mmol which corresonds with 1.58 grams of NaOH (4.94 grams of a 32 wt % solution). The mixture is then refluxed for an hour and then 50 mL MQ water is added and stirred until everything was dissolved. Next 5.62 grams of TBPBr (16.55 mmol) is dissolved in 25 mL MQ water and is added slowly to this solution and the product antistatic agent is formed. After all the dissolved TBPBr is added the mixture is stirred for another 15 minutes. Next the mixture is cooled down, preferably in an ice/water bath, and then the water is decanted. Then 100 mL MQ water is added and stirred for 15 minutes while heating it in an oil bath at 85° C. The mixture is cooled to room temperature and the product antistatic agent is isolated by filtration and flushed with 25 mL MQ water. The product antistatic agent is then dried in a vacuum drying oven at 50° C. The theoretical yield is 9.24 grams of antistatic agent; 5.8 grams were obtained.

Example 4

First 5.77 grams (18.083 mmol) of sodium perfluorobutane sulfonate ("Na Rimar") is added to and dissolved in 50 mL MQ water at room temperature and 6.08 (17.906 mmol) grams of TBPBr is added to and dissolved in 20 mL MQ water at room temperature. The TBPBr solution is filtered and then poured gradually into the Na Rimar salt solution while stirring with a strong magnetic stirrer, and the product antistatic agent is formed. After all the TBPBr is added the reaction mixture is stirred for 15 minutes more. At the end of the reaction the product antistatic agent is isolated by filtration and flushed with 50 mL MQ water to remove the most impurities. Further purification may be done by stirring the product antistatic agent in MQ water and heating it to 80° C., stirring it for a few minutes and cooling the mixture so that the product antistatic agent recrystallizes. The product antistatic agent is then isolated by filtration and dried in a vacuum drying oven at 50° C. The theoretical yield is 10.0 grams of antistatic agent; 8.10 grams were obtained.

Example 5

First, 5.00 grams (MW 302, 16.55 mmol) of perfluorobutane sulfonyl fluoride ("A") is weighed in a 100-mL 2-neck roundbottom flask, stirred with a magnetic stirrer and refluxed in an oil bath at 85° C. Next, 4.46 g of a 50 wt % KOH solution is slowly added to provide 2.4 equivalents of IKOH (2.23 g, 39.72 mmol) (4.46 gram of a 50 wt % solution). The mixture is refluxed for an hour and then 75 mL of ethanol/MQ (volume ratio of ¾) is added and stirred until everything has dissolved. Next 5.56 grams of TBPBr (16.38 mmol) is dissolved in 25 mL MQ water and added slowly to this solution and the product antistatic agent is formed. After all the dissolved TBPBr is added the mixture is stirred for another 15 minutes before cooling the mixture to room temperature. The product antistatic agent is extracted with 75 mL dichloromethane in a separatory funnel and washed 3 times with 50 mL MQ water. The organic layer is removed under vacumm (50° C., $p_{start}$=475 mbar and $P_{end}$=125 mbar). Additional purification may be accomplished by stirring the product antistatic agent in MQ water and heating it to 80° C., stirring for a few minutes, and cooling the mixture so that the product antistatic agent recrystallizes. The product antistatic agent is then isolated by filtration and dried in a vacuum drying oven at 50° C. The theoretical yield is 9.24 grams of antistatic agent; 6.04 grams were obtained.

Comparative Example 6

First, 6.06 grams (17.9 mmol) potassium perfluorobutane sulfonate ("K Rimar") is added to and dissolved in 75 mL of an ethanol/MQ water solution having a volume ratio of ¾ and 6.01 grams (17.7 mmol) of TBPBr is added to and dissolved in 25 mL MQ water at room temperature. The TBPBr solution is poured gradually into the K Rimar salt solution while stirring and the product antistatic agent is formed. After all the TBPBr is added, the reaction mixture is stirred for 15 minutes more. Then the product antistatic agent is extracted with 75 mL of dichloromethane in a separatory funnel and washed 3 times with 50 mL MQ water. The organic layer is removed under vacuum (50° C., $P_{start}$=475 mbar and $P_{end}$=125 mbar). Additional purification may be accomplished by stirring the product antistatic agent in MQ water and heating it to 80° C., stirring for a few minutes, and cooling the mixture so that the product antistatic agent recrystallizes. The product antistatic agent is then isolated by filtration and dried in a vacuum drying oven at 50° C. The theoretical yield is 10.0 grams of antistatic agent; 8.91 grams were obtained.

Example 7

First, 5.00 grams (MW 302, 16.55 mmol) of A is weighed in a 100-mL 2-neck roundbottom flask, stirred with a magnetic stirrer and refluxed in an oil bath at 85° C. Next, 10.98 grams (39.72 mmol) a 40 wt % tetrabutylphosphonium hydroxide is added. The mixture is then refluxed for an hour. Then 50 mL MQ water is added and stirred for another 15 minutes. The mixture is then cooled down, preferably in an ice/water bath, and then the water is decanted. Then 100 mL MQ water is added and stirred for 15 minutes while heating it in an oil bath at 85° C. This is followed by cooling the mixture down to room temperature, isolating the product antistatic agent by filtration and flushing it with 25 mL MQ water. Next the product antistatic agent is dried in a vacuum drying oven at 50° C. The theoretical yield herein is 9.24 grams of antistatic agent; 7.4 grams were obtained.

Table 1 provides the characterizations of the antistatic agents made via the various synthethic routes detailed above in Examples 1-7. The reference sample is a perfluorobutanesulfonate antistatic agent obtained from Dupont under the trade name Zonyl® FASP-1. The melting point is determined using differential scanning calorimetry (DSC). The thermal degradation of the the antistatic agent is determined by thermal gravimetric analysis (TGA) and is measured at the temperature wherein degradation is first detected.

TABLE 1

|  | Units | 1 | 2 | 3 | 4 | 5 | 6 | 7 | Ref. |
|---|---|---|---|---|---|---|---|---|---|
| Yield | % | 41.1 | 87.1 | 62.8 | 81.0 | 65.4 | 89.1 | 80.1 | — |
| Melting point (DSC) | ° C. | 77.5 | 75.9 | 77.6 | 77.4 | 75.1 | 78.0 | 77.3 | 76.7 |
| TGA Temperature onset | ° C. | 387 | 386 | 384 | 388 | 385 | 390 | 380 | 386 |

As may be seen from the above Table 1, the process of Example 3 is particularly advantageous, in that yields are high. In addition, the synthetic steps are simple.

Table 2 shows that the antistatic agent made via the various synthethic routes detailed in Examples 1-2 contains low ionic impurities after washing in water at 80° C.

TABLE 2

| | | Example No. | | | | | | | |
|---|---|---|---|---|---|---|---|---|---|
| Ion | Units | 1 | 2 | 3 | 4 | 5 | 6 | 7 | Ref. |
| $Li^+$ | ppm | <1 | <1 | <1 | <1 | <1 | <1 | <1 | <1 |
| $Na^+$ | ppm | <2 | <2 | <2 | <2 | <2 | <2 | <2 | <2 |
| $K^+$ | ppm | <2 | <2 | <2 | <2 | <2 | <2 | <2 | 2.1 |
| $F^-$ | ppm | <2 | <1 | <2 | <2 | <1 | <1 | 4.3 | <2 |
| $Cl^-$ | ppm | <2 | <1 | <2 | <2 | <1 | <1 | <2 | <2 |
| $Br^-$ | ppm | 85 | 10 | 4.6 | <2 | 81 | <1 | <4 | <4 |
| $SO_4^-$ | ppm | 3.5 | <1 | <2 | <1 | 6.7 | <2 | 2.8 | <2 |
| $PO_4^-$ | ppm | <6 | <1 | <6 | <1 | <4 | <4 | <6 | <6 |

As is known, certain byproducts commonly found in antistatic agent may be deleterious to the properties of the compounded thermoplastic polymers, for example polycarbonate. For example, as shown in FIG. 1, the presence of increasing amounts of bromine can result in increasing yellowing of the polycarbonate after heat aging at 130° C. for 936 hours. Table 3 further shows the change in YI (Delta YI), after heat aging, of polycarbonate containing the indicated amounts of ionic contaminants. Spots were observed in the heat-aged polycarbonate, which likely result from potassium and sodium contamination.

TABLE 3

| Ion concentration in PC (ppm) | | | | Delta YI after heat aging at 130° C. (Hours) | | | | |
|---|---|---|---|---|---|---|---|---|
| Br– | Li+ | Na+ | K+ | 0 | 65 | 166 | 569 | 936 |
| 0 | 0 | 0 | 0 | 0 | 0.7 | 1.1 | 3.3 | 5.6 |
| 0.1 | — | 0.1 | <0.15 | 0 | 0.6 | 1.1 | 2.8 | 5.1 |
| 12.4 | — | — | — | 0 | 0.7 | 1.7 | 3.9 | 6.2 |
| 21.8 | — | 1.0 | 1.4 | 0 | 0.6 | 1.8 | 4.6 | 8.1 |
| 22.5 | 2.1 | 0.1 | <0.15 | 0 | 1.1 | 2 | 5.2 | 9.4 |
| 24.7 | — | — | — | 0 | 0.9 | 1.8 | 5.8 | 10.5 |
| 37.0 | — | — | — | 0 | 1 | 1.9 | 8.7 | 19.1 |

In order to determine the effectiveness of washing the antistatic agents of the above examples, 10.02 grams of unwashed antistatic agent produced in Example 2 above is weighed into a 150 mL beaker and 100 mL MQ water is added. This is stirred so as to homogeneously disperse the antistatic agent in the water, and stirring is continued at room temperature for 15 minutes. The antistatic agent was then filtered, dried, and tested for ionic impurities.

In a second test, 10.06 grams of unwashed antistatic agent produced in Example 2 above is weighed into a 150 mL beaker and 100 mL MQ water is added thereto. This is stirred well so that the antistatic agent is homogeneously dispersed in the water, and stirring is continued at 80° C. for 15 minutes. At that temperature the antistatic agent of Example 2 is molten, and forms an emulsion while stirring. The mixture is then cooled, and the solid is filtered, dried, and tested for ionic impurities. Table 4 shows the yield after washing and Table 5 shows the ion chromatography results.

TABLE 4

| | | Washing | |
|---|---|---|---|
| | Units | At room temp. | At 80° C. |
| Amount before washing | gram | 10.02 | 10.06 |
| Amount of MQ water used | mL | 100 | 100 |
| Yield after washing | gram | 9.35 | 9.72 |
| Yiel after washing | % | 93.3 | 96.6 |

TABLE 5

| Ion | Units | Unwashed | Washed At room temp. | At 80° C. |
|---|---|---|---|---|
| $Li^+$ | Ppm | 279 | 16 | <1 |
| $Na^+$ | Ppm | <2 | <2 | <2 |
| $K^+$ | Ppm | <2 | <2 | <2 |
| $F^-$ | Ppm | 1.0 | <1 | <1 |
| $Cl^-$ | Ppm | <1 | <1 | <1 |
| $Br^-$ | Ppm | 2766 | 165 | 10 |
| $SO_4^-$ | Ppm | 14 | 2.3 | <1 |
| $PO_4^-$ | Ppm | <1 | <1 | <1 |

It is possible to synthesize the antistatic agent according to all the examples as described above. Any ionic impurities can be washed out easily by washing the antistatic agent in water at room temperature or at 80° C.

The singular forms "a," "an," and "the" include plural referents unless the context clearly dictates otherwise. The terms "first," "second," and the like, herein do not denote any order, quantity, or importance, but rather are used to distinguish one element from another. The endpoints of all ranges reciting the same characteristic are combinable and inclusive of the recited endpoint. The modifier "about" used in connection with a quantity is inclusive of the stated value and has the meaning dictated by the context (e.g., includes the degree of error associated with measurement of the particular quantity). All references are incorporated herein by reference.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

What is claimed is:

1. A method of preparing a thermoplastic composition, comprising:

preparing a phosphonium sulfonate salt of generic formula (1)

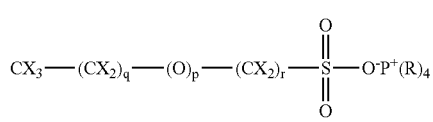
(1)

wherein each X is independently a halogen or hydrogen, provided that the molar ratio of halogen to hydrogen is greater than about 0.90; p is 0 or 1 and q and r are integers of 0 to about 7 provided that q+r is less than 8 and that if p is not zero then r is greater than zero; and each R is the same or different hydrocarbon radical containing 1 to about 18 carbon atoms; wherein preparing the phosphonium sulfonate salt comprises combining in an aqueous medium, a compound of the generic formula (2)

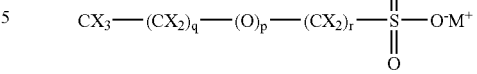
(2)

wherein M is Li or Na, and X, q, p, and r are as defined above, with a stoichiometric excess of a compound of the generic formula (3)

(3)

wherein Z is a halogen and R is as defined above; and
separating the phosphonium sulfonate of formula (1) from the aqueous medium;
wherein the aqueous medium comprises less than about 1 volume percent of a non-aqueous medium; and
combining the phosphonium sulfonate salt with a thermoplastic resin.

2. The method of claim 1 wherein the sulfonate is perfluoromethane sulfonate, perfluorobutane sulfonate, perfluorohexane sulfonate, perfluoroheptane sulfonate, perfluorooctane sulfonate, or a combination comprising at least one of the foregoing organic sulfonate anions; and wherein the phosphonium is tetrabutylphosphonium.

3. The method of claim 1, wherein separating phosphonium sulfonate from the aqueous medium comprises filtering precipitated phosphonium sulfonate from the aqueous medium.

4. The method of claim 1, wherein the thermoplastic resin is selected from the group consisting of polycarbonate, polyetherimide, polyester, polyphenylene ether/polystyrene blends, polyamides, polyketones, acrylonitrile-butadiene-styrenes, and combinations thereof.

5. The method of claim 1, wherein the thermoplastic resin is polycarbonate.

6. The method of claim 1, wherein combining the phosphonium sulfonate salt with the thermoplastic resin comprises using a phosphonium sulfonate salt amount of 0.01 to 10 weight percent, based on the weight of the thermoplastic resin.

7. A method of preparing a thermoplastic composition, comprising:

preparing a phosphonium sulfonate salt of generic formula (1)

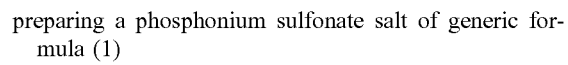
(1)

wherein each X is independently a halogen or hydrogen, provided that the molar ratio of halogen to hydrogen is greater than about 0.90; p is 0 or 1 and q and r are integers of 0 to about 7 provided that q+r is less than 8 and that if p is not zero then r is greater than zero; and each R is the same or different hydrocarbon radical containing 1 to about 18 carbon atoms; wherein preparing the phosphonium sulfonate salt comprises combining, in an aqueous medium, a compound of the generic formula (4)

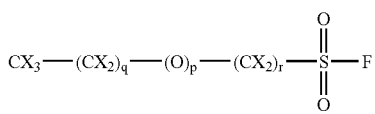 (4)

wherein X, p, q, and r have the same meanings as in formula (1), with a compound of the generic formula (5)

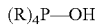 (5)

wherein R has the same meaning as in formula (1); and separating the phosphonium sulfonate product of formula (1); and combining the phosphonium sulfonate salt with a thermoplastic resin.

8. The method of claim 7 wherein the sulfonate is perfluoromethane sulfonate, perfluorobutane sulfonate, perfluorohexane sulfonate, perfluoroheptane sulfonate, perfluorooctane sulfonate, or a combination comprising at least one of the foregoing organic sulfonate anions; and wherein the phosphonium is tetrabutyiphosphonium.

9. The method of claim 7, wherein the thermoplastic resin is selected from the group consisting of polycarbonate, polyetherimide, polyester, polyphenylene ether/polystyrene blends, polyamides, polyketones, acrylonitrile-butadiene-styrenes, and combinations thereof.

10. The method of claim 7, wherein the thermoplastic resin is polycarbonate.

11. The method of claim 7, wherein combining the phosphonium sulfonate salt with the thermoplastic resin comprises using a phosphonium sulfonate salt amount of 0.01 to 10 weight percent, based on the weight of the thermoplastic resin.

\* \* \* \* \*